United States Patent [19]
Lacefield

[11] 3,948,894
[45] Apr. 6, 1976

[54] 3-AMINO-5,6-DIARYL-1,2,4-TRIAZINES
[75] Inventor: William B. Lacefield, Indianapolis, Ind.
[73] Assignee: Eli Lilly and Company, Indianapolis, Ind.
[22] Filed: Jan. 31, 1974
[21] Appl. No.: 438,156

[52] U.S. Cl.......... 260/249.5; 260/247.5 C; 424/249
[51] Int. Cl.² ...................................... C07D 253/06
[58] Field of Search ................................ 260/249.5

[56] References Cited
UNITED STATES PATENTS
2,653,933   9/1953   Erickson .......................... 260/249.5

OTHER PUBLICATIONS
Polonovski et al., *Comt.-Rend.* Vol. 232, pp. 1260–1262, (1951); *Chem. Abstr.* Vol. 46, 514(b), (1952).

*Primary Examiner*—John M. Ford
*Attorney, Agent, or Firm*—William B. Scanlon; Everet F. Smith

[57] ABSTRACT

This invention relates to certain 3-amino-5,6-diaryl-1,2,4-triazines useful as anti-inflammatory agents and a method of treating inflammation.

12 Claims, No Drawings

3-AMINO-5,6-DIARYL-1,2,4-TRIAZINES

BACKGROUND OF THE INVENTION

The etiology and pathogenesis of rheumatic and arthritic diseases remain obscure. Meanwhile the need continues for safer, better tolerated drugs which will slow the progress and alleviate the symptoms of these diseases. The 3-amino-5,6-diaryl-1,2,4-triazines of the present invention represent a novel class of nonsteroidal compounds useful in the treatment of the inflammatory processes.

The starting materials, intermediates and compounds of the invention are prepared by methods known to the art. The preparation of 5,6-diaryl-1,2,4-triazines is described by John G. Erickson in "The 1,2,3-And 1,2,4-Triazines, Tetrazines and Pentazines," The Chemistry of Heterocyclic Compounds, Vol. 10, Interscience Publishers, Inc., New York, N.Y., 1956, Chapter II, pp 44–84. The preparation of the 3-amino-5,6-diaryl-1,2,4-triazines by means of the amine nucleophilic displacement of a labile group at the 3-position of a 3-substituted-5,6-diaryl-1,2,4-triazine is known to the triazine and related pyrimidine art [see J. Amer. Chem. Soc. 78, 217 (1956)]. Alternatively, the compounds of the invention may be prepared by the condensation of 3,3-disubstituted aminoguanidines with the appropriate benzils. 3-Dimethylamino-5,6-bis-(4-methoxyphenyl)-1,2,4-triazine is described by Polonovski and Pesson, Compt. Rend, 232, 1260 (1951); Chem. Abstr. 46, 514 d (1952).

SUMMARY OF THE INVENTION

The present invention is directed to 3-amino-5,6-diaryl-1,2,4-triazine compounds of the formula

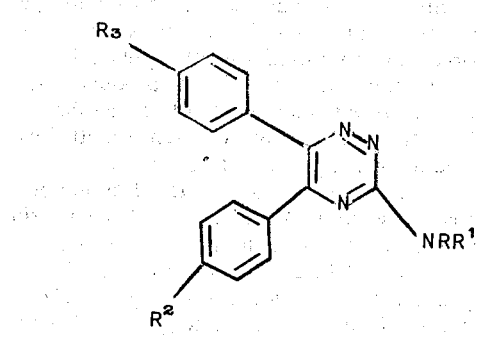

wherein R and $R^1$ when, taken separately are independently hydrogen, $C_1$–$C_3$ alkyl or —$CH_2CH(OH)$—$R^4$, $R^4$ being hydrogen, methyl or ethyl; R and $R^1$, when taken together with the nitrogen atom to which they are attached, represent a heterocyclic group; $R^2$ and $R^3$ are $C_1$–$C_3$ alkoxy, fluoro, dimethylamino or methyl sulfinyl; and the pharmaceutically acceptable acid addition salts thereof.

The compounds are prepared by the displacement of a labile group at the 3-position of a 3-substituted-5,6-diaryl-1,2,4-triazine with amines represented by the formula, $RR^1NH$.

In addition, the present invention relates to a method of treating inflammation and its concomitant swelling, fever and ossification in warm-blooded animals. More particularly, the present invention provides a method of treating inflammatory disorders which comprises orally administering a compound of the invention to a warm-blooded animal in a dose from 1 to 150 mg./kg. of animal body weight.

DETAILED DESCRIPTION OF THE INVENTION

The compounds provided by this invention are represented by the formula,

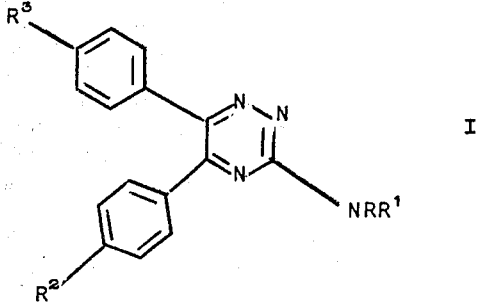

I wherein

R and $R^1$, when taken separately are hydrogen, $C_1$–$C_3$ alkyl or —$CH_2CH(OH)$—$R^4$, $R^4$ being hydrogen, methyl or ethyl;

R and $R^1$, when taken together with the nitrogen atom to which they are attached, are selected from the heterocyclic group consisting of
1. 4-($\beta$-hydroxyethyl)piperazino,
2. 4-hydroxypiperidino
3. 4-methylpiperazino
4. morpholino
5. piperidino and
6. pyrrolidino;

$R^2$ and $R^3$ are independently $C_1$–$C_3$ alkoxy, dimethylamino, fluoro or methylsulfinyl; subject to the limitations that
1. when one of R and $R^1$ is hydrogen, the other is —$CH_2CH(OH)$—$R^4$;
2. when $R^2$ is fluoro, $R^3$ is $C_1$–$C_3$ alkoxy;
3. when $R^3$ is fluoro, $R^2$ is $C_1$–$C_3$ alkoxy or dimethylamino; and
4. when $R^2$ and $R^3$ are both methoxy, one of R and $R^1$ is other than methyl;

and the pharmaceutically acceptable acid addition salts thereof.

The term "$C_1$–$C_3$ alkyl" includes methyl, ethyl, n-propyl, and isopropyl. The term "$C_1$–$C_3$ alkoxy" includes methoxy, ethoxy, n-propoxy, and isopropoxy.

Representative of the group —$CH_2CH(OH)$—$R^4$ are $\beta$-hydroxyethyl, $\beta$-hydroxypropyl, and $\beta$-hydroxybutyl.

The compounds of the invention are prepared in various ways. They are prepared in direct fashion by the reaction of 4-substituted or 4,4-disubstituted guanidines with the appropriate benzil starting materials. They are also prepared via 1,2,4-triazine intermediates bearing groups on the 3-position which are susceptible to nucleophilic displacement by amines. Another approach to the subject compounds involves the use of benzil starting materials bearing substituents which are converted to the desired groups, $R^2$ and $R^3$.

According to one method the 3-amino-5,6-diaryl-1,2,4-triazine compounds are prepared by reacting a 3-chloro 3-methoxy- or 3-methylthio-5,6-diaryl-1,2,4-triazine precursor with amines, $RR^1NH$, via nucleophilic displacement of the labile group on the 3-position. The starting materials in this method are prepared as follows: The appropriate benzil starting materials are condensed with semicarbazide or its hydrochloride to provide 3-hydroxy-5,6-diaryl-1,2,4-triazine intermediates. The 3-hydroxytriazines are converted to the corresponding 3-chlorotriazines by reaction with phosphorous oxychloride. Methanolysis of the 3-chlorotriazine under basic conditions provides the 3-methoxytriazine intermediates. Benzil condensations with thiosemicarbazide provide 5,6-diaryl-1,2,4-triazine-3-thiols which are converted to the corresponding 3-methylthiotriazine intermediates by alkylation with methyliodide under basic conditions. For example, the reaction of 4,4'-fluorobenzil with thiosemicarbazide provides a 5,6-bis(4-fluorophenyl)-1,2,4-triazine-3-thiol intermediate which is converted to the 3-methylthio derivative and thereafter to 5-(4-dimethylaminophenyl)-6-(4-fluorophenyl)-3-methylthio-1,2,4-triazine via displacement of the 4-fluoro group on the phenyl moiety in the 5-position by reaction with dimethylamine. 4,4'-Methylthiobenzil provides 3-amino-5,6-bis (4-methylthiophenyl)-1,2,4-triazines which are oxidized by m-perbenzoic acid to 3-amino-5,6-bis(4-methylsulfinylphenyl)-1,2,4-triazines.

The benzils required for the triazine intermediates are prepared by the oxidation of benzoins obtained from aromatic aldehydes via reaction with cyanide ion, i.e., the classic benzoin condensation [See Organic Reactions 4, 269 (1948)]. The resultant benzoins are oxidized to benzils with copper sulfate in pyridine as described by Clarke and Driger, Organic Synthesis, Coll. Vol. I, 87 (1941), for example.

Unsymmetrical benzils are obtained from mixed benzoins which arise when dissimilar aldehydes are condensed. The benzil compounds required for the preparation of the starting materials and intermediate triazines are represented by the formula

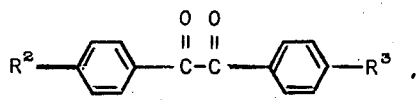

wherein $R^2$ and $R^3$ are described hereinabove. When $R^2$ and $R^3$ represent different groups the depicted benzils are unsymmetrical. The use of unsymmetrical benzil starting materials may result in the preparation of isomer mixtures of triazines. For example, the condensation of 4-dimethyl-amino-4'-methoxybenzil with thiosemicarbazide provides a mixture of 5-(4-dimethylaminophenyl)-6-(4-methoxyphenyl)-1,2,4-triazine-3-thiol and 6-(4-dimethylaminophenyl)-5-(4-methoxyphenyl)-1,2,4-triazine-3-thiol. 4-Dimethylamino-4'-fluorobenzil is an unsymmetrical benzil which condenses with guanidines or semicarbazides to form predominantly one isomer, a 5-(4-dimethylaminophenyl)-6-(4-fluorophenyl)-3-substituted-1,2,4-triazine.

It will be recognized by those skilled in the art that isomeric mixtures of triazine salts or free bases are separable by methods such as fractional crystallization or chromatography. The isomer separation may be effected upon intermediate mixtures or delayed until the final product stage. While it is preferable to employ the pure triazine isomers as anti-inflammatory agents, the mixtures are also useful for the purpose mentioned herein in accordance with their antiphlogistic content.

The reactant amines, represented by the formula, $RR^1NH$, are employed neat, in excess, at their boiling temperatures to accomplish the nucleophilic displacements. The required alkyl- and carbinolamines which are not commercially available are prepared by the methods known to the art, i.e., the alkylation of ammonia, the reduction of cyanides, nitro compounds and oximes, reductive alkylation, the Curtius reaction, the Gabriel amine synthesis, the Hofmann reaction, the Leuckart reaction, the Schmid reaction, etc. The nucleophilic amines, in excess or molar equivalent amounts, are also used in the presence of inert solvents such as alcohols, benzene, dioxane, pyridine, toluene, xylene and the like. Volatile amines are reacted in a sealed autoclave. In the halogen displacement of 3-chlorotriazines, it is convenient to employ excess amine, since the amine also serves as the halo-acid scavenger. Acid scavengers such as pyridine, triethylamine, sodium carbonate and the like are used with a molar equivalent of the amine in an inert solvent when the amine may be an economic consideration.

The instant 3-amino-5,6-diaryl-1,2,4-triazines are relatively weak bases; however, they form acid-addition salts with strong acids. The compounds of the invention which contain one or more dimethylamino groups on the phenyl rings form salts more readily, since their basicity is of the order of dimethylaniline. The pharmaceutically-acceptable salts are readily prepared in the conventional manner by treating the compound in the free base form with the appropriate acid. Representative of such salts are the hydrochloride, hydrobromide, nitrate, sulfate, phosphate, toluenesulfonate and the like.

The following examples illustrate the various aspects of the invention and the preferred embodiments thereof. A preferred method of preparing the compounds of the invention is the displacement of the labile group on the 3-position of a 3-chloro- or 3-methylthio triazine precursor with amines of the formula $HNRR^1$. Thus, for example, 3-chloro-5,6-bis(4-methoxyphenyl)-1,2,4-triazine is reacted with diisopropanolamine in ethanol at reflux temperature to give 3-diisopropanolamino-5,6-bis(4-methoxyphenyl)-1,2,4-triazine after recovery of the product. 3-(N-Methyl-N-$\beta$-hydroxyethylamino)-5,6-bis(4-methoxyphenyl)-1,2,4-triazine is obtained when 3-methylthio-5,6-bis(4-methoxyphenyl)-1,2,4-triazine is reacted with excess N-methylethanolamine at reflux temperature. Similarly, reaction of the 3-methylthio triazine precursor with excess anhydrous dimethylamine at 150°C. for about 12 hours in an autoclave provides 3-dimethylamino-5,6-bis(4-methoxyphenyl)-1,2,4-triazine. 5,6-bis(4-Dimethylamino-phenyl)-3-(4-hydroxypiperidino)-1,2,4-triazine is obtained when 5,6-bis(4-dimethylaminophenyl)-3-methylthio-1,2,4-triazine and 4-hydroxypiperidine are heated at about 150°C. for 12 hours.

A double nucleophilic displacement is employed to prepare the compounds of the invention wherein the substituent on the 5-phenyl ring is dimethylamino and that on the 6-phenyl moiety is fluoro. The 4-fluoro group on the phenyl moiety on the 5-position of 5,6-bis(4-fluorophenyl)-3-substituted-1,2,4-triazines is susceptible to displacement with dimethylamine. In fact, that particular fluoro group is more readily displaced than the labile groups on the 3-position on the triazine. The fluorine atom is displaced with excess ethanolic dimethylamine at room temperature in an autoclave with retention of the 3-methylthio group. Fluorine displacement provides the 3-methylthio-5-(4-dimethylaminophenyl)-6-(4-fluorophenyl)-1,2,4-triazine precursor which is further reacted with appropriate amines to provide the desired compounds. Concomitant displacement occurs when 5,6-bis(4-fluorophenyl)-3-methylthio-1,2,4-triazine is reacted with excess anhydrous dimethylamine at 100°C. for 12 hours in an autoclave. The reaction product is conventionally isolated to provide 3-dimethylamino-5-(4-dimethylaminophenyl)-6-(4-fluorophenyl)-1,2,4-triazine.

An oxidation procedure is employed to provide the compounds of the invention which contain methylfulfinyl groups. Thus, for example, 3-dimethylamino-5,6-bis(4-methyl-thiophenyl)-1,2,4-triazine is oxidized with m-chloroperbenzoic acid at a temperature of −80°C. in dichloroethane. After the oxidation reaction is completed, the mixture is decomposed with saturated sodium carbonate solution to yield 3-dimethyl-amino-5,6-bis(4-methylsulfinylphenyl)-1,2,4-triazine. Similarly, 3-methylthio-5,6-bis(4-methylthiophenyl)-1,2,4-triazine is oxidized to 3-methylthio-5,6-bis(4-methylsulfinyl-phenyl)-1,2,4-triazine.

In addition, the instant invention concerns a method of treating inflammation and its concomitant swelling, fever and ossification in warm-blooded animals. In particular this invention provides a method of treating inflammatory disorders which comprises orally administering to a warmblooded animal from 1 to 100 mg./kg. of animal body weight a compound of the invention represented by the Formula I.

A modification of the Winder method was used to measure the anti-inflammatory -activities of the instant triazines (Winder, C. V.; Wax, J.; Burr, V.; Been, M.; and Posiere, C. E.; A Study of Pharmacological Influences on Ultraviolet Erythema in Guinea Pigs. Arch. Int. Pharmcodyn. 116: 261, 1958). Albino guinea pigs of either sex, weighing 225–300 grams, were shaved on the back and chemically depilated 18–20 hours before exposure to ultraviolet light (Nair, Lotion Hair Remover, Carter Products, N. Y., N. Y.). The animals were fasted overnight. A group of 50 animals bearing identifying ear tags were dosed by means of an oral dosing needle. The drugs were administered as suspensions in 1 to 2 cc. of methyl cellulose (Methocell, Dow). The control treatment consisted of administering only the drug vehicle, Methocell, to a group of four animals. A positive control treatment consisted of giving four animals an effective dose of fenoprofen, 2-(3-phenoxyphenyl)propionic acid. Ten groups of four animals each were given different dose levels of test compound to obtain dose-responses. Random order and blind administration of the drugs were employed. All 48 animals were graded, and drug identification was made after the animals were graded. The test was considered invalid if the animals gave abnormal responses to fenoprofen. Immediately after the guinea pigs were treated, a gummed notebook paper reinforcement was placed on their backs, and they were exposed to a high intensity ultraviolet light for 7 seconds. The ultraviolet light source, a Hanovia Lamp (Kromayer-Model 10), was placed in contact with the skin of the guinea pig's back. After exposure, the reinforcements were removed, and the back was wiped clean with a water-soaked gauze sponge. The unexposed area under the reinforcement provided an area of contrast for grading the erythema. Beginning one hour after exposure and thereafter at half-hour intervals for another 1½ hours, the degree of resulting erythema was graded by an arbitrary scoring system based upon the degree of contrast and redness formed. Anti-inflammatory agents delay the development of the erythema and usually have their greatest effect at the initial grading periods. The scores were, therefore, weighted by factors of 4, 3, 2, and 1 at the 1.0, 1.5, 2.0, and 2.5 hour scoring times, respectively. The erythema was graded as follows:

| Score | Erythema Scoring System<br>Appearance of Exposed Area |
|---|---|
| 0 | No redness and no contrast |
| 1 | Slight redness with a faint reinforcement outline |
| 2 | Slight to moderate redness with a distinct outline |
| 3 | Marked redness with a distinct circular outline |

Total scores from each treatment group of four guinea pigs were compared to the control treatment, and the percent inhibition was calculated as follows:

$$100 \times \frac{\text{Control Score} - \text{Treatment Score}}{\text{Control Score}} = \text{Percent Inhibition}$$

A dose-repose graph was obtained by plotting dose versus percent inhibition, the points representing the average of each treatment group of four guinea pigs. The dose ($ED_{50}$) in milligrams per kilogram (mg./kg.) of animal body weight which produced a 50% inhibition of the erythemic response for the particular compound tested was obtained by extrapolation. Table I below summarizes the results obtained from testing representative compounds of the invention by the foregoing method. The plotted dose ($ED_{50}$) which represents a 50% inhibition of the erythemic response for the particular compound tested is given in the last column of Table I.

A preferred group of compounds provided by this invention are those wherein the phenyl rings are substituted by $C_1$–$C_3$ alkoxy or dimethylamino. Among the preferred compounds, an especially preferred group are those wherein one or both of R and $R^1$ are —$CH_2$CH(OH)—$R^4$ as exemplified by 3-ethanolamino-5,6-bis(4-methoxyphenyl)-1,2,4-triazine, 3-[N-methyl-N-(β-hydroxyethyl)amino]-5,6-bis(4-methoxyphenyl)-1,2,4-triazine and 3-diisopropylamino-5,6-bis(4-methoxy-phenyl)-1,2,4-triazine.

A further preferred group of compounds wherein R and $R^1$, taken together, are a heterocyclic group and the phenyl rings are substituted by $C_1$–$C_3$ alkoxy or dimethylamino, is exemplified by 5,6-bis(4-methoxyphenyl)-3-(4-methylpiperazino)-1,2,4-triazine and 5,6-bis(4-dimethylaminophenyl)-3-(4-hydroxy-piperidino)-1,2,4-triazine.

The preferred compounds, in addition to being anti-inflammatory agents, are analgesics and increase the pain threshold in rats in the Randall-Selitto carrageenan assay. In addition they inhibit writhing induced by acetic acid in mice. The preferred compounds are also antipyretics which lower yeast-induced fever in rats, presumably by the inhibition of prostaglandins in a manner similar to the action of aspirin [see Nature 239, 33 (1972)]. Some of the preferred compounds of the invention also inhibit platelet aggregation in vivo and may be useful as antithrombotic agents.

Table I.

Erythemic response of
3-amino-5,6-diaryl-1,2,4-triazines
of formula I

| NRR¹ | R² | R³ | $Ed_{50}$ mg/kg |
|---|---|---|---|
| N(CH₃)CH₂CH₂OH | OCH₃ | OCH₃ | 4 |
| N(C₂H₅)CH₂CH₂OH | OCH₃ | OCH₃ | 4 |
| N(CHCHOHCH₃)₂ | OCH₃ | OCH₃ | 4 |
| N(CH₃)₂ | OCH₃ | OCH₃ | 8 |
| N(CH₂CH₂OH)₂ | OCH₃ | OCH₃ | 10 |
| NHCH₂CH₂OH | OCH₃ | OCH₃ | 16 |
| 4-methylpiperazino | OCH₃ | OCH₃ | 16 |
| morpholino | OCH₃ | OCH₃ | 25 |
| pyrrolidino | OCH₃ | OCH₃ | 25 |
| N(CH₃)₂ | N(CH₃)₂ | F | 28 |
| N(C₂H₅)₂ | OCH₃ | OCH₃ | 30 |
| piperidino | OCH₃ | OCH₃ | 35 |
| N(CH₃)₂ | N(CH₃)₂ | N(CH₃)₂ | 13 |
| N(CH₃)₂ | S(O)CH₃ | S(O)CH₃ | 50 |
| 4-hydroxypiperidino | N(CH₃)₂ | N(CH₃)₂ | 3 |
| N(CH₃)CH₂CH₂OH | N(CH₃)₂ | N(CH₃)₂ | 13 |
| N(n-C₃H₇)CH₂CH₂OH | OCH₃ | OCH₃ | 8 |
| 4-(β-hydroxyethyl)-piperazino | OCH₃ | OCH₃ | 35 |
| 4-hydroxypiperidino | OCH₃ | OCH₃ | 33 |

The toxicity of representative triazines, determined as the dose ($LD_{50}$) in milligrams per kilogram (mg./kg.) of animal body weight which is lethal to 50 percent of mice treated by the intraperitoneal route, lies between 300 and 1000 mg./kg. 3-Dimethylamino-5,6-bis(4-methoxyphenyl)-1,2,4-triazine has an $LD_{50}$ greater than 1000 mg./kg. in mice.

This invention provides a method of treating inflammation, and the resulting pain and fever in humans and animals by employing a 3-amino-5,6-diaryl-1,2,4-triazine as the anti-inflammatory agent.

In the practice of this invention, one of the compounds is orally administered to a warm-blooded animal in a dose of 1 to 150 mg./kg. of animal body weight. The administration can be repeated periodically as needed. In accordance with general practice, the anti-inflammatory triazine compound can be administered every four to six hours. While oral administration is the preferred route of administration, the anti-inflammatory agents disclosed herein can also be administered parenterally or as rectal suppositories.

Preferably, the compounds to be employed in accordance with the present invention are employed in combination with one or more adjuvants suited to the particular route of administration. Thus, in the case of oral administration, the compound is modified with pharmaceutical diluents or carriers such as lactose, sucrose, starch powder, cellulose, talc, magnesium stearate, magnesium oxide, calcium sulfate, acacia powder, gelatin, sodium alginate, sodium benzoate and stearic acid. Such compositions can be formulated as tablets or enclosed in capsules for convenient administration. The compounds can also be mixed with a liquid and administered as elixirs, suspensions, and the like. In the case of parenteral administration, the compound to be used is conveniently formulated in saline to constitute an injectable liquid solution. Other adjuvants and modes of administration are known to those skilled in the art.

Illustrative of the triazine compounds which are provided by this invention are the following:

5-(4-dimethylaminophenyl)-3-(β-hydroxybutylamino)-6-4-methylsulfinylphenyl)-1,2,4-triazine 5-(4-dimethylaminophenyl)-3-ethanolamino-6-(4-methoxy-phenyl)-1,2,4-triazine 3-(4-hydroxypiperidino)-6-(4-methoxyphenyl)-5-(4-methyl-sulfinylphenyl)-1,2,4-triazine 3-dimethylamino-6-(4-methylsufinylphenyl)-5-(4-dimethyl-aminophenyl)-1,2,4-triazine 6-(4-isopropoxyphenyl)-5-(4-methoxyphenyl)-3-[4-(β-hydroxy-ethyl)piperazino]-1,2,4-triazine 3-dimethylamino-5,6-bis(4-ethoxyphenyl)-1,2,4-triazine 3-(4-methylpiperazino)-5,6-bis(4-methylsulfinylphenyl)-1,2,4-triazine 3-diisopropylamino-5,6-bis(4-methylsulfinylphenyl)-1,2,4-triazine 6-(4-ethoxyphenyl)-5-(4-methoxyphenyl)-3-pyrrolidino-1,2,4-triazine 5,6-bis(4-methylsulfinylphenyl)-3-piperidino-1,2,4-triazine 3-diisopropanolamino-5,6-bis(4-isopropoxyphenyl)-1,2,4-triazine 6-(4-dimethylaminophenyl)-3-[4-(β-hydroxyethyl)-piperazino]-5-(4-propoxyphenyl)-1,2,4-triazine 5-(4-ethoxyphenyl)-3-(4-hydroxypiperidino)-6-(4-methoxy-phenyl)-1,2,4-triazine 6-(4-dimethylaminophenyl)-5-(4-methoxyphenyl)-3-(4-methyl-piperazino)-1,2,4-triazine 6-(4-isopropoxyphenyl)-3-[N-propyl-N-(β-hydroxypropyl)-amino]-5-(4-methoxyphenyl)-1,2,4-triazine 3-diisopropylamino-5-(4-dimethylaminophenyl)-6-(4-ethoxy-phenyl)-1,2,4-triazine 6-(4-dimethylaminophenyl)-3-[4-(β-hydroxyethyl)-piperazino]-5-(4-methoxyphenyl)-1,2,4-triazine 6-(4-dimethylaminophenyl)-3-dimethylamino-5-(4-methoxy-phenyl)-1,2,4-triazine 5-(4-dimethylamino)-3-dimethylamino-6-(4-methoxyphenyl)-1,2,4-triazine 6-(4-ethoxyphenyl)-3-[N-(β-hydroxybutyl)-N-(isopropyl)-amino]-5-(4-methoxyphenyl)-1,2,4-triazine 6-(4-dimethylaminophenyl)-3-diisopropylamino-5-(4-isopro-poxyphenyl)-1,2,4-triazine 5-(4-dimethylaminophenyl)-3-(β-hydroxybutylamino)-6-(4-methoxyphenyl)-1,2,4-triazine 6-(4-dimethylaminophenyl)-3-(4-hydroxypiperazino)-5-(4-methoxyphenyl)-1,2,4-triazine 3-[N-methyl-N-(β-hydroxyethyl)amino]-5,6-bis(4-isopropoxyphenyl)-1,2,4-triazine 3-dimethylamino-6-(4-dimethylaminophenyl)-5-(4-methyl-sulfinylphenyl)-1,2,4-triazine 5-(4-dimethylaminophenyl)-3-ethanolamino-6-(4-methyl-sulfinylphenyl)-1,2,4-triazine 6-(4-dimethylaminophenyl)-3-(4-hydroxypiperidino)-5-(4-methylsulfinylphenyl)-1,2,4-triazine 3-dimethylamino-6-(4-ethoxyphenyl)-5-(4-methyl-sulfinyl-phenyl)-1,2,4-triazine 3-dimethylamino-5-(4-ethoxyphenyl)-6-(4-methyl-sulfinyl-phenyl)-1,2,4-triazine 3-diisopropylamino-5-(4-isopropoxyphenyl)-6-(4-methyl-sulfinylphenyl)-1,2,4-triazine 6-(4-dimethylaminophenyl)-5-(4-methylsulfinylphenyl)-3-pyrrolidino-1,2,4-triazine 3-(4-methylpiperazino)-5-(4-methylsulfinylphenyl)-6-(4-methoxyphenyl)-1,2,4-triazine 6-(4-ethoxyphenyl)-3-(β-hydroxybutylamino)-5-(4-methyl-sulfinylphenyl)-1,2,4-triazine 6-(4-dimethylaminophenyl)-3-[N-(β-hydroxyethyl)-N-methyl-amino]-5-(4-methylsulfinylphenyl)-1,2,4-triazine 5-(4-dimethylaminophenyl)-3-[N-(β-hydroxyethyl)-N-methyl-amino]-6-(4-methylsulfinylphenyl)-1,2,4-triazine 6-(4-dimethylaminophenyl)-3-[N-(β-hydroxyethyl)-N-methyl-amino]-5-(4-methylsulfinylphenyl)-1,2,4-triazine 3-diisopropylamino-5-(4-methylsulfinylphenyl)-6-(4-methoxyphenyl)-1,2,4-triazine 3-dimethylamino-5-(4-fluorophenyl)-6-(4-methoxyphenyl)-1,2,4-triazine 3-dimethylamino-6-(4-fluorophenyl)-5-(4-methoxyphenyl)-1,2,4-triazine 3-diisopropylamino-5-(4-fluorophenyl)-6-(4-ethoxyphenyl)-1,2,4-triazine 3-ethanolamino-6-(4-fluorophenyl)-5-(4-propoxyphenyl)-1,2,4-triazine 5-(4-fluorophenyl)-3-(4-hydroxypiperidino)-6-(4-isopropoxyphenyl)-1,2,4-triazine 6-(4-fluorophenyl)-3-[N-(β-hydroxyethyl)-N-isopropylamino]-5-(4-methoxyphenyl)-1,2,4-triazine 3-diisopropylamino-5-(4-fluorophenyl)-6-(4-ethoxyphrnyl)-1,2,4-triazine 6-(4-fluorophenyl)-3-(N-methyl-N-isopropylamino)-5-(4-ethoxyphenyl)-1,2,4-triazine 5-(4-fluorophenyl)-3-(N-ethyl-N-propylamino)-6-(4-propoxy-phenyl)-1,2,4-triazine 3-(dipropylamino-6-(4-fluorophenyl)-5-(4-methoxyphenyl)-1,2,4-triazine 5-(4-fluorophenyl)-3-diethylamino-6-(4-isopropoxyphenyl)-1,2,4-triazine 6-(4-fluorophenyl)-3-(N-methyl-N-ethylamino)-5-(4-methoxy-phenyl)-1,2,4-triazine 3-(N-methyl-N-propylamino)5,6-bis(4-ethoxyphenyl)-1,2,4-triazine 3-(N-methyl-N-isopropylamino)-5,6-bis(4-methoxyphenyl)-1,2,4-triazine 5,6-bis(4-dimethylaminophenyl)-3-[4-(β-hydroxyethyl)-piperazino]-1,2,4-triazine 5,6-bis(4-dimethylaminophenyl)-3-(4-hydorxypiperidino)-1,2,4-triazine 5,6-bis(4-dimethylaminophenyl)-3-pyrrolidino-1,2,4-triazine 5,6-bis(4-dimethylaminophenyl)-3-morpholino-1,2,4-triazine 5,6-bis(4-dimethylaminophenyl)-3-piperidino-1,2,4-triazine 3-[N-(β-hydroxyethyl)-N-methylamino]-5,6-bis(4-dimethyl-aminophenyl)-1,2,4-triazine 3-[N-ethyl-N-(β-hydroxyethyl)amino]-5,6-bis(4-dimethyl-aminophenyl)-1,2,4-triazine 3-[N-(β-hydroxyethyl)-N-propylamino]-5,6-bis(4-dimethyl-amino)-1,2,4-triazine 3-[N-(β-hydroxyethyl)-N-isopropylamino]-5,6-bis(4-dimethyl-aminophenyl)-1,2,4-triazine 3-diisopropanolamino-5,6-bis(4-dimethylaminophenyl)-1,2,4-triazine 3-[N-(β-hydroxyethyl)-N-methylamino]-5,6-bis(4-methyl-sulfinylphenyl)-1,2,4-triazine 3-[N-ethyl-N-(β-hydroxyethyl)amino]-5,6-bis(4-methyl-sulfinylphenyl)-1,2,4-triazine 3-[N-(β-hydroxyethyl)-N-propylamino]-5,6-bis(4-methyl-sulfinylphenyl)-1,2,4-triazine 3-[N-(β-hydroxyethyl)-N-isopropylamino]-5,6-bis(4-methyl-sulfinylphenyl)-1,2,4-triazine 3-diisopropanolamino-5,6-bis(4-methylsulfinylphenyl)-1,2,4-triazine 3-[N-(β-hydroxyphenyl)-N-methylamino]-5,6-bis(4-methyl-sulfinylphenyl)-1,2,4-triazine 3-[N-(β-hydroxypropyl)amino]-5,6-bis(4-methylsulfinyl-phenyl)-1,2,4-triazine 3-[-[N-(β-hydroxypropyl)-N-isopropylamino]-5,6-bis(4-methyl-sulfinylphenyl)-1,2,4-triazine 3-diethanolamino-5,6-bis(4-methylsulfinylphenyl)-1,2,4-triazine 3-(β-hydroxybutyl)amino-5,6-bis(4-methylsulfinylphenyl)-1,2,4-triazine 3-[4-(β-hydroxyethyl)piperazino]-5,6-bis(4-methyl-sulfinyl-phenyl)-1,2,4-triazine 3-(4-hydroxypiperidino)-5,6-bis(4-methylsulfinylphenyl)-1,2,4-triazine 3,(4-morpholino)-5,6-bis(4-methylsulfinylphenyl)-1,2,4-triazine 3-piperidino-5,6-bis(4-methylsulfinylphenyl)-1,2,4-triazine 5-(4-dimethylaminophenyl)-6-(4-fluorophenyl)-3-ethanolamino-1,2,4-triazine 5-(4-dimethylaminophenyl)-6-(4-fluorophenyl)-3-(4-hydroxy-piperidino)-1,2,4-triazine 5-(4-dimethylaminophenyl)-6-(4-fluorophenyl)-3-(4-methyl-piperazino)-1,2,4-triazine 5-(4-dimethylaminophenyl)-6-(4-fluorophenyl)-3-morpholino-1,2,4-triazine 5-(4-dimethylaminophenyl)-6-(4-fluorophenyl)-3-pyrrolidino-1,2,4-triazine 5-(4-dimethylaminophenyl)-6-(4-fluorophenyl)-3-piperidino-1,2,4-triazine 5-(4-dimethylaminophenyl)-6-(4-methoxyphenyl)-5-morpholino-1,2,4-triazine 5-(4-dimethylaminophenyl)-6-(4-methoxyphenyl)-3-pyrrolidino-1,2,4-triazine 5-(4-dimethylaminophenyl)-6-(4-methoxyphenyl)-3-piperidino-1,2,4-triazine 3-diisopropanolamino-5-(4-isopropoxyphenyl)-6-(4-methoxy-phenyl)-1,2,4-triazine The following examples further illustrate the preparation of the starting materials, intermediates, and compounds of my invention.

EXAMPLE 1

Preparation of 3-Diisopropanolamino-5,6-bis(4-methoxyphenyl)-1,2,4-triazine

A. 3-Hydroxy-5,6-bis(4-methoxyphenyl)-1,2,4-triazine.-

Two moles, 540 g., of anisil (4,4'-dimethoxybenzil), 222 g. (2 moles) of semicarbazide hydrochloride, 180 g. (2.2 moles) of sodium acetate and 2.5 liters of acetic acid were refluxed overnight. The cooled reaction mixture was poured into 5 liters of water. The crude solid product was collected by filtration, washed with water and recrystallized from acetic acid. The yield was 434 g. of 3-hydroxy-5,6-bis(4-methoxyphenyl)-1,2,4-triazine, mp about 272°–274°C.

| Analysis: | $C_{17}H_{15}N_3O_3$ |
|---|---|
| Calc: | C, 66.01; H, 4.89; N, 13.58 |
| Found: | C, 65.92; H, 5.04; N, 13.66 |

B. 3-Chloro-5,6-bis(4-methoxyphenyl)-1,2,4-triazine.-

Ten grams of 3-hydroxy-5,6-bis(4-methoxyphenyl)-1,2,4-triazine and 50 ml. of phosphorous oxychloride were refluxed for 1.5 hours. The cooled mixture was poured onto crushed ice and the resultant mixture was extracted with ether. The extract was washed successively with 2 percent sodium hydroxide and water until the washings were neutral. The ether extract was dried over anhydrous sodium sulfate and evaporated. The residue was taken up in ether, filtered and the filtrate was evaporated to yield 9.0 g. of 3-chloro-5,6-bis(4-methoxyphenyl)-1,2,4-triazine, mp about 130°–132°C.

| Analysis: | $C_{17}H_{14}ClN_3O_2$ |
|---|---|
| Calc: | C, 62.30; H, 4.31; Cl, 10.82; N, 12.82 |
| Found: | C, 62.50; H, 4.48; Cl, 10.53; N, 12.99 |

C. 3-Diisopropanolamino-5,6-bis(4-methoxyphenyl)-1,2,4-triazine.

Ten grams (0.03 mole) of 3-chloro-5,6-bis(4-methoxy-phenyl)-1,2,4-triazine, 75 ml. of ethanol and 8 g. (0.66 mole) of diisopropanolamine were refluxed for 4 hour. Water was added to the cooled reaction mixture. The mixture was extracted with ether-ethyl acetate (1:1) and the extract was washed with water and saturated sodium chloride solution. The extract was dried over anhydrous sodium sulfate and evaporated to an oil which was taken up in ether. Evaporation of the ether gave a crystalline solid and a dark oil. The oil was decanted and the solid was recrystallized from ether to yield 2.6 g. of 3-diisopropanolamino-5,6-bis(4-methoxyphenyl)-1,2,4-triazine, mp about 148°–149°C. A second crop, 2.6 g., mp about 147°–149°C., was obtained.

| Analysis: | $C_{23}H_{28}N_4O_4$ |
|---|---|
| Calc: | C, 65.08; H, 6.65; N, 13.20 |
| Found: | C, 64.80; H, 6.43; N, 13.06 |

EXAMPLES 2–3

The following compounds were prepared by the method of Example 1 using the appropriate amines and 3-chloro-5,6-bis(4-methoxyphenyl)-1,2,4-triazine prepared by the method of Example 1(B):

3-(N-ethyl-N-β-hydroxyethylamino)-5,6-bis(4-methoxy-phenyl)-1,2,4-triazine, mp about 95°–97°C.

| Analysis: | $C_{21}H_{24}N_4O_3$ |
|---|---|
| Calc: | C, 66.30; H, 6.36; N, 14.73 |
| Found: | C, 66.26; H, 6.59; N, 14.65 |

3-(N-propyl-N-β-hydroxyethylamino)-5,6-bis(4-methoxy)-1,2,4-triazine, mp about 94°–98°C.

| Analysis: | $C_{22}H_{26}N_4O_3$ |
|---|---|
| Calc: | C, 66.99; H, 6.64; N, 14.20 |
| Found: | C, 66.98; H, 6.64; N, 14.43 |

EXAMPLE 4

Preparation of 3-Ethanolamino-5,6-bis(4-methoxyphenyl)-1,2,4-triazine

A. 3-mercapto-5,6-bis(4-methoxyphenyl)-1,2,4-triazine.-

One hundred grams of anisil (4,4'-dimethoxybenzil) were added to 600 ml. of acetic acid and the mixture was heated to about 100°C. with stirring. Thiosemicarbazide, 68.4 g., was added and the mixture was refluxed for about an hour. The mixture was cooled and the solid product was collected by filtration. The solid was washed with acetic acid and water. The product was filtered and air dried to yield 96.3 g. of 3-mercapto-5,6-bis(4-methoxyphenyl)-1,2,4-triazine, mp about 233°–236°C.

| Analysis: | $C_{17}H_{15}N_3O_2S$ |
|---|---|
| Calc: | C, 62.75; H, 4.65; N, 12.91; S, 9.85 |
| Found: | C, 62.61; H, 4.57; N, 12.66; S, 9.73 |

B. 3-Methylthio-5,6-bis(4-methoxyphenyl)-1,2,4-triazine,-

Eight grams (0.20 mole) of sodium hydroxide were dissolved in 600 ml. of ethanol by warming. The basic solution was cooled to room temperature and 67.0 grams (0.20 mole) of 3-mercapto-5,6-bis(4-methoxyphenyl)-1,2,4-triazine were added. Methyl iodide, 67 g. (0.47 mole), was added to the reaction mixture and the mixture immediately became a slurry. Three hundred milliliters of ethanol were added to the slurry and stirring was continued for about 3 hours. One hundred milliliters of water were added to the reaction mixture and the solid product was collected by filtration. The yield of 3-methylmercapto-5,6-bis(4-methoxyphenyl)-1,2,4-triazine, mp about 152°–155°C., was 67.3 g.

| Analysis: | $C_{18}H_{17}N_3O_2S$ |
|---|---|
| Calc: | C, 63.70; H, 5.05; N, 12.38 |
| Found: | C, 63.82; H, 5.31; N, 12.10 |

C. 3-Ethanolamino-5,6-bis(4-methoxyphenyl)-1,2,4-triazine.-

Ten grams of 3-methylmercapto-5,6-bis(4-methoxyphenyl)-1,2,4-triazine and 50 ml. of ethanolamine were refluxed for 12 hours. The mixture was cooled and water was added to the point of incipient turbidity. Crystallization of the product was completed upon standing. The solid product was filtered and recrystallized from ethanol to yield 3.8 g. of 3-ethanolamino-5,6-bis(4-methoxyphenyl)-1,2,4-triazine, mp about 175°–179°C.

| Analysis: | $C_{19}H_{20}N_4O_3$ |
|---|---|
| Calc: | C, 64.76; H, 5.72; N, 15.90 |
| Found: | C, 64.70; H, 5.90; N, 16.12 |

EXAMPLES 5–9

The following compounds were prepared by the method of Example 4 using the appropriate amines and 3-methylthio-5,6-bis(4-methoxyphenyl)-1,2,4-triazine prepared by the method of Example 4(B):

3-Diethanolamino-5,6-bis(4-methoxyphenyl)-1,2,4-triazine, mp about 125°–127°C.

| Analysis: | $C_{21}H_{24}N_4O_4$ |
|---|---|
| Calc: | C, 63.62; H, 6.10; N, 14.13 |
| Found: | C, 63.39; H, 6.36; N, 13.91 |

3-Dimethylamino-5,6-bis(4-methoxyphenyl)-1,2,4-triazine, mp about 132°–135°C., was prepared using anhydrous dimethylamine in a sealed autoclave at a temperature of 150°C. for 12 hours.

| Analysis: | $C_{19}H_{20}N_4O_2$ |
|---|---|
| Calc: | C, 67.84; H, 5.99; N, 16.66 |
| Found: | C, 67.85; H, 6.14; N, 16.67 |

3-Morpholino-5,6-bis(4-methoxyphenyl)-1,2,4-triazine, mp about 127°–130°C.

| Analysis: | $C_{21}H_{22}N_4O_3$ |
|---|---|
| Calc: | C, 66.65; H, 5.86; N, 14.81 |
| Found: | C, 66.41; H, 5.75; N, 14.60 |

3-Piperidino-5,6-bis(4-methoxyphenyl)-1,2,4-triazine, mp about 133°–135°C.

| Analysis: | $C_{22}H_{24}N_4O_2$ |
|---|---|
| Calc: | C, 70.19; H, 6.42; N, 14.88 |
| Found: | C, 69.92; H, 6.27; N, 14.57 |

3-(N-methyl-N-β-hydroxyethylamino)-5,6-bis(4-methoxy-phenyl)-1,2,4-triazine, mp about 108°–111°C.

| Analysis: | $C_{20}H_{22}N_4O_3$ |
|---|---|
| Calc: | C, 65.56; H, 6.05; N, 15.29 |
| Found: | C, 65.33; H, 6.30; N, 15.39 |

EXAMPLE 10

Preparation of 3-dimethylamino-5,6-bis(4-methylsulfinylphenyl)-1,2,4-triazine

A. 3-Mercapto-5,6-bis(4-methylthiophenyl)-1,2,4-triazine.-

Forty grams of 4,4'-methylthiobenzil were reacted with 48 g. of thiosemicarbazide by the method of Example 4(A) to yield 36 g. of 3-mercapto-5,6-bis(4-methylthiophenyl)-1,2,4-triazine, mp about 225°–230°C., with decomposition.

| Analysis: | $C_{17}H_{15}N_3S_3$ |
|---|---|
| Calc: | C, 57.11; H, 4.23; N, 11.75; S, 26.91 |
| Found: | C, 56.87; H, 4.37; N, 11.45; S, 27.03 |

B. 3-Methylthio-5,6-bis(4-methylthiophenyl)-1,2,4-triazine.-

Thirty-six grams (0.10 mole) of 3-mercapto-5,6-bis(4-methylthiophenyl)-1,2,4-triazine were reacted with 14 g. (0.10 mole) of methyl iodide in 1000 ml. of ethanol containing 4.2 g. of sodium hydroxide by the method of Example 4(B) to yield 31 g. of 3-methylthio-5,6-bis(4-methylthiophenyl)-1,2,4-triazine, mp about 149°–51°C., which was characterized by nuclear magnetic resonance spectrum (NMR).

| Analysis: | $C_{18}H_{17}N_3O_3$ | MW 371 |
|---|---|---|
| Calc: | C, 58.19; H, 4.61; N, 11.31; S, 25.89 | |
| Found: | C, 58.25; H, 4.58; N, 11.60; S, 25.76 | |

C. 3-Dimethylamino-5,6-bis(4-methylthiophenyl)-1,2,4-triazine.-

Ten grams of 3-methylthio-5,6-bis(4-methylthiophenyl)-1,2,4-triazine were reacted with 100 g. of anhydrous dimethyl-amine in an autoclave at 150°C. for 12 hours. After venting the autoclave, the cooled reaction mixture was taken up in ethanol and was evaporated in vacuo to an oil which solidified on standing. The solid residue was taken up in ethanol and crystallized to yield 3.1 g. of 3-dimethylamino-5,6-bis(4-methylthiophenyl)-1,2,4-triazine, mp about 141°–143°C.

| Analysis: | $C_{19}H_{20}N_4S_2$ |
|---|---|
| Calc: | C, 61.92; H, 5.47; N, 15.20; S, 17.40 |
| Found: | C, 61.64; H, 5.57; N, 14.95; S, 17.16 |

D. 3-Dimethylamino-5,6-bis(4-methylsulfinylphenyl)-1,2,4-triazine.-

3-Dimethylamino-5,6-bis(4-methylthiophenyl)-1,2,4-triazine, 11.04 g. (0.03 mole), was dissolved in 100 ml. of dichloroethane and the mixture was cooled to −80°C. in a dry ice-acetone bath. m-Chloroperbenzoic acid, 11.28 g. (0.06 mole), dissolved in dichloroethane, was added dropwise to the cold, stirred mixture. The reaction temperature rose to −30°C. over the next hour after the peracid addition was completed. The reaction mixture was allowed to come to room temperature. The mixture was diluted with dichloroethane and washed with saturated sodium carbonate solution. The organic phase was washed with water until the washings were neutral. The dichloroethane solution was dried (MgSO$_4$) and evaporated in vacuo to yield 10.5 g. of oil. The oil was taken up in ethanol and crystallization was induced by cooling the solution. The product was filtered and recrystallized from ethanol to yield 3.5 g. of 3-dimethylamino-5,6-bis(4-methylsulfinylphenyl)-1,2,4-triazine, mp about 205°–211°C; an infrared spectrum of the compound showed sulfoxide absorption at 950$^{-1}$ cm. A second crop, 2.0 g., mp about 199°–204°C., and a third crop, 2.1 g., mp about 182°–185°C., were obtained.

| Analysis: | $C_{19}H_{20}N_4O_2S$ | MW 400 |
|---|---|---|
| Calc: | C, 56.98; H, 5.03; N, 13.99; S, 16.01 | |
| Found: | C, 56.70; H, 4.89; N, 13.95; S, 15.74 | |

EXAMPLE 11

Preparation of 3-dimethylamino-5-(4-dimethyl-aminophenyl)-6-(4-fluorophenyl)-1,2,4-triazine A. 4,4'-Fluorobenzil.

One mole, 148 g., of 4-fluorobenzaldehyde and 20 g. of sodium cyanide in 100 ml. of water were refluxed in one liter of ethanol for 1.5 hours. The reaction mixture was diluted with 3 volumes of water and the product was extracted into ether. The ether extract was washed with water and dried (Na$_2$SO$_4$). The ether was evaporated in vacuo and the residue was taken up in etherhexane (1:1). The product crystallized upon cooling to yield 63 g. of 4,4'-fluorobenzoin, mp about 72°–73°C.

| Analysis: | $C_{14}H_{10}F_2O_2$ |
|---|---|
| Calc: | C, 67.74; H, 4.06 |
| Found: | C, 67.66; H, 4.33 |

Sixty three grams (0.225 mole) of 4,4'-fluorobenzoin, 100 g. of copper sulfate, 135 ml. of pyridine and 45 ml. of water were refluxed for 2 hours. The reaction mixture was poured into 2 liters of water and ice. The aqueous mixture was extracted with ether. The ether extract was washed successively with water, dilute hydrochloric acid, water and dried ($Na_2SO_4$). The ether was evaporated in vacuo. The residue was crystallized from dilute ethanol to yield 47 g. of 4,4'-fluorobenzil, mp about 110°–112°C., yellow needles.

| Analysis: | $C_{14}H_8F_2O_2$ |
|---|---|
| Calc: | C, 68.30; H, 3.28 |
| Found: | C, 68.44; H, 3.47 |

B.   3-Mercapto-5,6-bis(4-fluorophenyl)-1,2,4-triazine.-

Eighty grams of 4,4'-fluorobenzil in 400 ml. of ethanol were reacted with 80 g. of thiosemicarbazide and 96 g. of sodium acetate by the method of Example 4(A) to yield 57.5 g. of 3-mercapto-5,6-bis(4-fluorophenyl)-1,2,4-triazine, mp about 180°–182°C. after recrystallization from acetic acid.

| Analysis: | $C_{15}H_9F_2N_3S$ |
|---|---|
| Calc: | C, 59.79; H, 3.01; N, 13.95 |
| Found: | C, 59.96; H, 3.12; N, 14.05 |

C.   3-Methylthio-5,6-bis(4-fluorophenyl)-1,2,4-triazine.-

3-Mercapto-5,6-bis(4-fluorophenyl)-1,2,4-triazine, 16.6 g. (0.05 mole), was reacted with 7 g. (0.05 mole) of methyl iodide in 75 ml. of ethanol containing 2 g. (0.05 mole) of sodium hydroxide by the method of Example 4(B). The yield was 13.2 g. of 3-methylthio-5,6-bis(4-fluorophenyl)-1,2,4-triazine, mp about 132°–135°C., after crystallization from ethanol.

| Analysis: | $C_{16}H_{11}F_2N_3S$ |
|---|---|
| Calc: | C, 60.90; H, 3.52; N, 13.33 |
| Found: | C, 60.67; H, 3.71; N, 13.13 |

D. 3-Dimethylamino-5-(4-dimethylaminophenyl)-6-(4-fluoro-phenyl)-1,2,4-triazine.-

Five grams of 3-methylthio-5,6-bis(4-fluorophenyl)-1,2,4-triazine were reacted with 100 g. of anhydrous dimethylamine in 100 ml. of ethanol at 100°C. for 12 hours in an autoclave. The autoclave was vented and the reaction mixture was evaporated in vacuo. The residue was recrystallized from ethanol. An NMR spectrum of the solid showed that the para fluoro group on the benzene moiety in the 5-position of the triazine had been replaced by dimethylamine. The yield was 4.7 g. of 3-dimethylamino-5-(4-dimethylaminophenyl)-6-(4-fluorophenyl)-1,2,4-triazine, mp about 157°–160°C.

| Analysis: | $C_{19}H_{20}N_5F$ |
|---|---|
| Calc: | C, 67.64; H, 5.98; N, 20.76; F, 5.63 |
| Found: | C, 67.60; H, 5.91; N, 20.53; F, 5.72 |

EXAMPLE 12

3-Dimethylamino-5,6-bis(4-dimethyl-aminophenyl)-1,2,4-triazine

A.   5,6-bis(4-Dimethylaminophenyl)-3-mercapto-1,2,4-triazine.-

4,4'-Dimethylaminobenzil, 13.4 g. (0.045 mole), was suspended in 200 ml. of acetic acid and the mixture was warmed to 90°C. Thiosemicarbazide, 6.4 g. (0.07 mole), was added and the mixture was refluxed for 2 hours. During that time the insoluble product came out of solution. The reaction mixture was stirred overnight at room temperature. The solid product was collected by filtration. The product was washed successively with alcohol, water, alcohol and finally, chloroform. The yield was 6.1 g. of 5,6-bis(dimethylaminophenyl)-3-mercapto-1,2,4-triazine, mp about 276°–279°C.

| Analysis: | $C_{19}H_{21}N_5S$ | MW 357.47 |
|---|---|---|
| Calc: | C, 64.93; H, 6.02; N, 19.93 | |
| Found: | C, 64.83; H, 6.02; N, 20.18 | |

B.   5,6-bis(dimethylaminophenyl)-3-methylthio-1,2,4-triazine.-

Sodium hydroxide, 0.68 g. (0.017 mole), was dissolved in 50 ml. of ethanol. Six grams (0.017 mole) of 5,6-bis(4-dimethylaminophenyl)-3-mercapto-1,2,4-triazine was added to the basic mixture along with 25 ml. of ethanol. A trace of insoluble material was filtered. Methyl iodide, 2.7 g. (0.019 mole), was added to the clear filtrate and the mixture was stirred overnight. The insoluble product was filtered and recrystallized from ethanol to yield 3.1 g. of 5,6-bis(dimethyl-aminophenyl)-3-methylthio-1,2,4-triazine, mp about 161°–163°C.

| Analysis: | $C_{20}H_{23}N_5S$ | MW 365.5 |
|---|---|---|
| Calc: | C, 65.72; H, 6.34; N, 19.16 | |
| Found: | C, 65.62; H, 6.23; N, 18.87 | |

C.   3-Dimethylamino-5,6-bis(4-dimethylaminophenyl)-1,2,4-triazine.-

Five grams of 5,6-bis(dimethylaminophenyl)-3-methyl-thio-1,2,4-triazine and 50 ml. of anhydrous dimethylamine were placed in an autoclave which was then sealed. The mixture was heated at 150°C. for 12 hours. The autoclave was vented and the reaction product was washed out of the autoclave with ethanol. The alcoholic solution was filtered and the filtrate was evaporated. The solid residue was recrystallized from ethanol to yield 3.2 g. of 3-dimethylamino-5,6-bis(4-dimethyl-aminophenyl)-1,2,4-triazine, mp about 170°–172°C.

| Analysis: | $C_{21}H_{26}N_6$ | MW 362.48 |
|---|---|---|
| Calc: | C, 69.58; H, 7.23; N, 23.19 | |
| Found: | C, 69.32; H, 6.96; N, 23.01 | |

EXAMPLE 13

Preparation of
5,6-bis(4-methoxyphenyl)-3-[4-(β-hydroxyethyl)-piperazino]-1,2,4-triazine Ten grams of 5,6-bis(4-methoxyphenyl)-3-methylthio-1,2,4-triazine and 20 ml. of N-β-hydroxyethyl-piperazine were heated at about 150°C. for 12 hours. The reaction mixture was treated with water and the water decanted. The residue was taken up in a minimum amount of ethanol and cooled. The product was collected and recrystallized from ethanol to yield 3.3 grams of 5,6-bis(4-methoxyphenyl)-3-[4-(β-hydroxyethyl)piperazine]-1,2,4-triazine, mp about 151°–153°C.

| Analysis: | $C_{23}H_{27}N_5O_3$ | MW 421.50 |
|---|---|---|
| Calc: | C, 65.54; H, 6.46; N, 16.62. | |
| Found: | C, 65.79; H, 6.52; N, 16.37. | |

EXAMPLE 14

Preparation of
5,6-bis(4-dimethylaminophenyl)-3-(4-hydroxypiperidino)-1,2,4-triazine Three grams of 5,6-bis(4-dimethylaminophenyl)-3-methylthio-1,2,4-triazine and 1.5 g. of 4-hydroxypiperidine were heated at about 150°C. for 12 hours. The reaction mixture was treated with water and the product was collected. The product was dissolved in benzene and the solution was slowly added to n-hexane. The solid which precipitated was recrystallized from ethyl acetate to yield 1.6 g. of 5,6-bis(4-dimethylaminophenyl)-3-(4-hydroxypiperidine-1,2,4-triazine, mp about 186°–188°C.

| Analysis: | $C_{24}H_{30}N_6$ | MW 418.54 |
|---|---|---|
| Calc: | C, 68.87; H, 7.23; N, 20.08 | |
| Found: | C, 68.66; H, 6.97; N, 19.93 | |

EXAMPLE 15

Preparation of
3-(4-methylpiperazino)-5,6-bis(4-methoxy-phenyl)-1,2,4-triazine

Ten grams of 5,6-bis(4-methoxyphenyl)-3-methylthio-1,2,4-triazine and 40 ml. of N-methylpiperazine were refluxed for 12 hours. The reaction mixture was poured into water and the solid product was collected. The product was crystallized twice from 75 ml. of ethanol and twice from ethyl acetate to yield 1.8 g. of 3-(4-methylpiperazino)-5,6-bis(4-methoxy-phenyl)-1,2,4-triazine, mp about 158°–160°C.

| Analysis: | $C_{22}H_{25}N_5O_2$ | |
|---|---|---|
| Calc: | C, 67.50; H, 6.44; N, 17.89 | |
| Found: | C, 67.41; H, 6.58; N, 17.64 | |

EXAMPLE 16

Preparation of
3-(4-hydroxypiperidino)-5,6-bis(4-methoxyphenyl)-1,2,4-triazine

Ten grams of 5,6-bis(4-methoxyphenyl)-3-methylthio-1,2,4-triazine was added to 15 g. of 4-hydroxypiperidine. The reaction mixture was maintained at about 150°C. for 8 hours. The melt was cooled and treated with water. A gummy solid precipitated from the aqueous mixture. The aqueous phase was decanted and the gummy solid was taken up in ethanol. The ethanol solution was filtered and the filtrate was evaporated to give an amorphous solid. A crystalline material was obtained when the amorphous solid was treated with water. The crystalline material was taken up in ethyl acetate. The ethyl acetate solution was washed successively twice with 100 ml. of 0.1 M hydrochloric acid and water and dried ($Na_2SO_4$). The solvent was evaporated in vacuo and the residue was crystallized from aqueous ethanol. The yield was 2.9 g. of 3-(4-hydroxy-piperidino)-5,6-bis(4-methoxyphenyl)-1,2,4-triazine, mp about 105°–108°C.

| Analysis: | $C_{22}H_{24}N_4O_3$ | |
|---|---|---|
| Calc: | C, 67.33; H, 6.16; N, 14.28. | |
| Found: | C, 66.93; H, 6.32; N, 14.07. | |

I claim:
1. The compound of the formula:

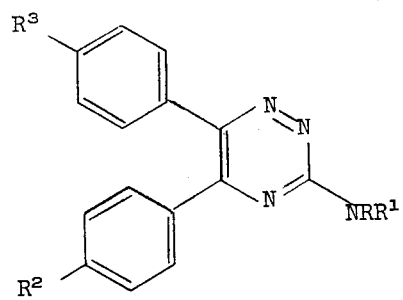

wherein
R and $R^1$, when taken separately are hydrogen, $C_1$–$C_3$ alkyl or —$CH_2CH(OH)$—$R^4$, $R^4$ being hydrogen, methyl or ethyl;
R and $R^1$, when taken together with the nitrogen atom to which they are attached, are selected from the heterocyclic group consisting of
 1. 4-(β-hydroxyethyl)piperazino,
 2. 4-hydroxypiperidino,
 3. 4-methylpiperazino,
 4. piperidino and
 5. pyrrolidino;
$R^2$ and $R^3$ are independently $C_1$–$C_3$ alkoxy, dimethylamino, fluoro and methylsulfinyl;
and the pharmaceutically acceptable acid addition salts thereof; subject to the limitations that
 1. when one of R and $R^1$ is hydrogen, the other is —$CH_2CH(OH)$—$R^4$;
 2. when $R^2$ is fluoro, $R^3$ is $C_1$–$C_3$ alkoxy;
 3. when $R^3$ is fluoro, $R^2$ is $C_1$–$C_3$ alkoxy or dimethylamino; and 4. when $R^2$ and $R^3$ are both methoxy, one of R and $R^1$ is other than methyl.

2. The compound of claim 1 wherein $R^2$ and $R^3$ are $C_1$–$C_3$ alkoxy or dimethylamino.

3. The compound of claim 2 wherein R and $R^1$ are hydrogen, $C_1$–$C_3$ alkyl or —$CH_2CH(OH)$—$R^4$, $R^4$ being hydrogen, methyl or ethyl.

4. The compound of claim 3 which is 3-dimethylamino-5,6-bis(4-dimethylaminophenyl)-1,2,4-triazine.

5. The compound of claim 3 wherein at least one of R and $R^1$ is —$CH_2CH(OH)$—$R^4$.

6. The compound of claim 5 which is 3-ethanolamino-5,6-bis(4-methoxyphenyl)-1,2,4-triazine.

7. The compound of claim 5 which is 3-[N-ethyl-N-($\beta$-hydroxyethyl)amino]-5,6-bis(4-methoxyphenyl)-1,2,4-triazine.

8. The compound of claim 5 which is 3-diisopropanolamino-5,6-bis(4-methoxyphenyl)-1,2,4-triazine.

9. The compound of claim 5 which is 3-[N-methyl-N-($\beta$-hydroxyethyl)amino]-5,6-bis(4-methoxyphenyl)-1,2,4-triazine.

10. The compound of claim 2 wherein R and $R^1$, when taken together with the nitrogen atom to which they are attached are a heterocyclic group.

11. The compound of claim 10 which is 4,5-bis(4-dimethylaminophenyl)-3-(4-hydroxypiperidino)-1,2,4-triazine.

12. The compound of claim 10 which is 3-(4-methylpiperazino)-5,6-bis(4-methoxyphenyl)-1,2,4-triazine.

* * * * *